United States Patent [19]

Smith et al.

[11] Patent Number: 5,643,311
[45] Date of Patent: Jul. 1, 1997

[54] UTERINE MANIPULATOR AND MANIPULATOR TIP ASSEMBLY

[75] Inventors: Steven R. Smith, Draper; Christopher A. Cutler, Centerville; William D. Wallace, Salt Lake City, all of Utah

[73] Assignee: Clinical Innovation Associates, Inc., Murray, Utah

[21] Appl. No.: 532,898

[22] Filed: Sep. 22, 1995

Related U.S. Application Data

[62] Division of Ser. No. 148,840, Nov. 5, 1993, Pat. No. 5,487,377.

[51] Int. Cl.$^6$ .......................... A61H 29/02; A61B 1/313; A61B 1/303
[52] U.S. Cl. .................. 606/193; 606/192; 604/96; 600/205; 600/207; 600/210
[58] Field of Search .................. 600/204, 205, 600/206, 207, 208, 210, 235, 187, 190; 606/119, 191, 192, 193; 604/55, 96

[56] References Cited

U.S. PATENT DOCUMENTS

| | | |
|---|---|---|
| 1,856,295 | 5/1932 | Sovatkin . |
| 2,186,143 | 1/1940 | Neugass . |
| 2,456,806 | 12/1948 | Wolffe . |
| 2,482,622 | 9/1949 | Kahn . |
| 2,723,666 | 11/1955 | Greenberg . |
| 3,131,690 | 5/1964 | Innis, et al. . |
| 3,153,267 | 10/1964 | Rowland . |
| 3,766,909 | 10/1973 | Ozbey . |
| 3,809,091 | 5/1974 | Shute . |
| 3,877,433 | 4/1975 | Librach . |
| 3,948,270 | 4/1976 | Hasson . |
| 4,000,743 | 1/1977 | Weaver ...................... 606/119 |
| 4,022,208 | 5/1977 | Valtchev . |
| 4,066,071 | 1/1978 | Nagel . |
| 4,085,756 | 4/1978 | Weaver . |
| 4,089,337 | 5/1978 | Kronner . |
| 4,323,057 | 4/1982 | Jamieson . |
| 4,430,076 | 2/1984 | Harris . |
| 4,459,978 | 7/1984 | Kotsanis . |
| 4,562,832 | 1/1986 | Wilder et al. . |
| 4,597,030 | 6/1986 | Brody et al. . |
| 4,627,421 | 12/1986 | Symbas et al. . |
| 4,664,114 | 5/1987 | Ghodsian ...................... 606/192 |
| 4,775,362 | 10/1988 | Kronner . |
| 4,996,974 | 3/1991 | Ciarlei . |
| 4,997,419 | 3/1991 | Lakatos et al. . |
| 5,007,898 | 4/1991 | Rosenbluth et al. ............ 606/192 X |
| 5,100,382 | 3/1992 | Valtchev . |
| 5,104,377 | 4/1992 | Levine . |
| 5,178,133 | 1/1993 | Pena . |

(List continued on next page.)

FOREIGN PATENT DOCUMENTS

| | | |
|---|---|---|
| 2078526A | 1/1982 | United Kingdom . |
| 9312709 | 7/1993 | WIPO . |

OTHER PUBLICATIONS

Bard Reproductive Systems brochrue entitled "Bard Uterine Manipulator", 2 pp. 1990.
Cook OB/Gyn brochure entitled "Majoli Uterine Manipulator/Injector", 1 p. 1992.
Conklin Surgical Instruments Ltd. brochure entitled "The Valtcheve Uterine Mobilizer", 2 pp; (undated but illustrative of a prior art device).
Storz brochure entitled "Uterine cannula and Elevator", 1 p. and accompanying descriptive text (1 p). 1990.

*Primary Examiner*—Beverly M. Flanagan
*Attorney, Agent, or Firm*—Trask, Britt & Rossa

[57] ABSTRACT

A disposable uterine manipulator including a pivotable tip support at the distal end of an elongated insertion rod for carrying a manipulator tip assembly, the tip support being rotatable by a manual drive at the proximal end of the insertion rod via a drive linkage to effectuate a range of rotation of the tip support of at least greater than 90° anteversion and at least greater than 30° retroversion. The manual drive may be an articulated linkage, a belt drive, or an axle drive. Several designs for a manipulator tip assembly including a balloon and a dye injection passage are also disclosed.

9 Claims, 6 Drawing Sheets

U.S. PATENT DOCUMENTS

| | | |
|---|---|---|
| 5,195,505 | 3/1993 | Josefsen . |
| 5,195,506 | 3/1993 | Hulfish . |
| 5,195,964 | 3/1993 | Kletzky et al. . |
| 5,217,466 | 6/1993 | Hasson . |
| 5,237,985 | 8/1993 | Hogdson et al. . |
| 5,338,297 | 8/1994 | Kocur et al. .................... 606/193 X |
| 5,382,252 | 1/1995 | Failla et al. . |
| 5,409,496 | 4/1995 | Rowden et al. .................. 128/20 X |
| 5,460,610 | 10/1995 | Michael .......................... 606/192 X |

UTERINE MANIPULATOR AND MANIPULATOR TIP ASSEMBLY

This is a division of application Ser. No. 08/148,840, filed Nov. 5, 1993, now U.S. Pat. No. 5,487,377.

BACKGROUND OF THE INVENTION

1. Field of the Invention

The present invention pertains generally to medical instrumentation, and more specifically to a device for moving the uterus (along with adnexa) to different positions for better visualization and surgical access.

2. State of the Art

Some type of uterine manipulator is currently deemed essential by practitioners for all laparoscopies involving the female pelvic organs (uterus, tubes, ovaries) when a uterus is present, as surgery without a uterine manipulator is more dangerous and can be more time consuming. Exemplary laparoscopies in which a uterine manipulator has substantial utility include: tubal ligations; diagnostic laparoscopies for evaluating pelvic pain and infertility; treatment of endometriosis, removal of pelvic scars (adhesions) involving the uterus, fallopian tubes and ovaries; treatment of ectopic pregnancy; removal of uterine fibroids; removal of ovarian cysts; removal of ovaries; tubal repair; laparoscopic hysterectomy, laparoscopic repair of pelvic bowel or bladder; sampling of pelvic lymph nodes; "tying up" the bladder to prevent urine loss; and biopsy of pelvic masses.

Uterine manipulators are also employed as conduits for the delivery of dye into the uterus when the physician wishes to obtain a picture of the uterus (hysterosalpingogram), and has become an important feature of manipulators. However, due to poor design, dye leakage through the cervix is very common, which may cause imaging problems as well as interfering with the procedure.

Figure 1:
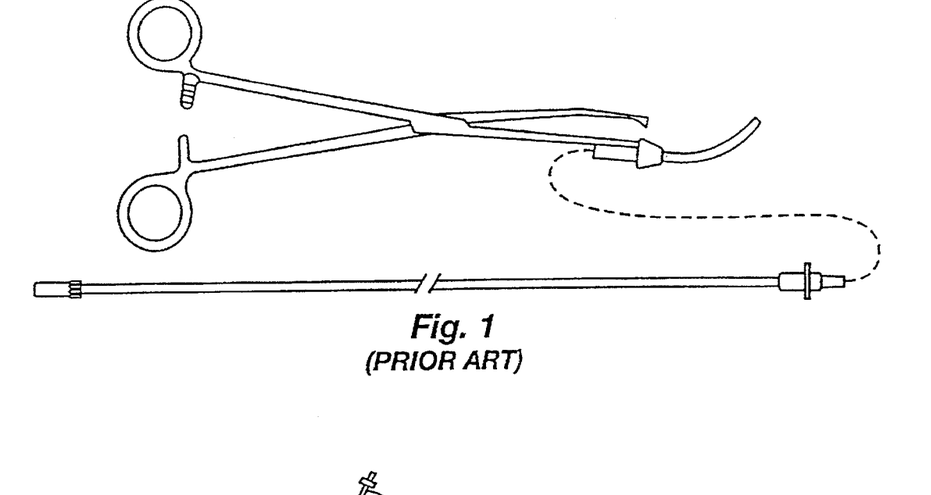
FIG. 1 is a side elevation of a Majoli uterine manipulator.

Most state of the art manipulators are merely rigid instruments which attach in a fixed manner to the uterus and protrude from the vagina. The instrument is typically held in place by sharp hooks embedded in the cervix, such as with a tenaculum. A typical example of such prior art devices is the Majoli Uterine Manipulator/Injector, sold by Cook Urological, Inc. of Spencer, Ind. (see FIG. 1). The handle of the instrument is grasped outside the vagina, and uterine manipulation is effected by applying torque to the rigid handle of the device at a point some distance from the organ. The uterus typically may be elevated only 45° from the vaginal axis, or lowered 10°–15°. The capability for movement to the right or left is minimal, and pelvic tissues and organs are unnecessarily stressed by application of excessive torque. Exposure of the vital regions of the pelvis is difficult, and surgery with such instruments is often suboptimal or even unsafe. Further, such devices and methods routinely require an extra staff member to maintain the instrument in the correct position to perform a procedure. In some cases this is very cumbersome, and obviously adds time and cost to the procedure.

One of the most significant complications of the aforementioned type of manipulator is tearing of the cervix with the tenaculum as the manipulator is adjusted and positioned, causing persistent and occasionally extensive bleeding. Such problems occur most often with inexperienced or inadequately trained personnel. The end result is longer operating room time with associated expense, as well as longer patient recovery and concern caused to the patient due to vaginal bleeding.

Another potential complication is uterine perforation resulting from excessive force being exerted by the physician when trying to place the manipulator into the uterus or during attempted manipulation of the uterus for better visualization. While infrequent, such an occurrence may convert the procedure from a laparoscopy to a laparotomy.

In an attempt to avoid the above problems, a class of manipulators has been developed which use a balloon inflated at the distal end of the instrument after the instrument has been inserted to perform the function of the tenaculum. Examples are the Harris Uterine Manipulator Injector (HUMI) disclosed in U.S. Pat. No. 4,430,076, and similar devices marketed as the Zinnanti Uterine Manipulator Injector (ZUMI) and the Kronner manipulator. The HUMI was the first plastic, disposable manipulator. The HUMI uses an intrauterine balloon and external spring and stop at the cervical os. Another device of this type, which uses two balloons mounted on a long, stiff metal rod, one inside and one outside of the uterus, is marketed by C.R. Bard, Inc. of Tewksbury, Mass.

Figure 2A:
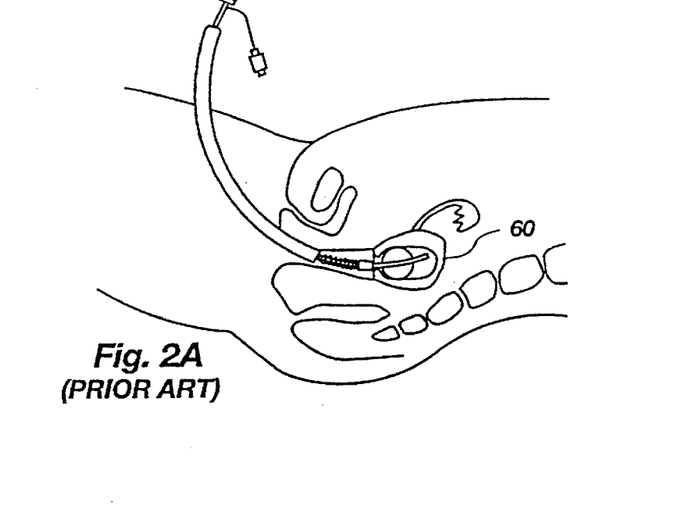
FIGS. 2A and 2B are schematic illustrations of a HUMI-type uterine manipulator in use.
Figure 2B:
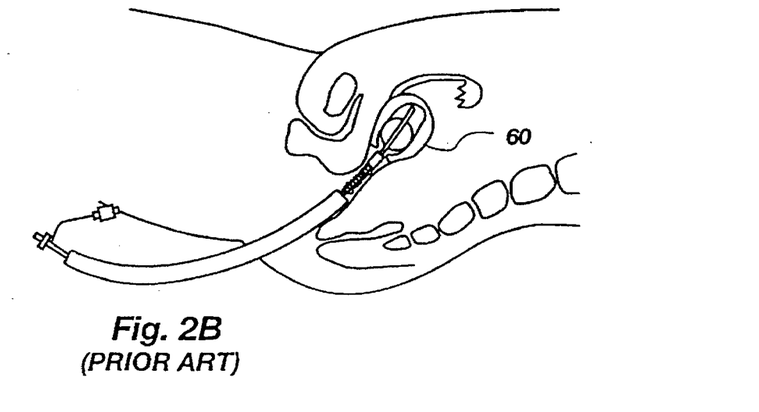

A major drawback with this class of devices is the lack of good manipulatory control. Without a pivot point at the cervical opening, these instrument are severely limited in their effective range of motion, in part due to the shape of the device itself and in part due to the configuration of such devices, which limits manipulation due to contact with the table on which the patient is placed or contact between the patient and the instrument. The cannula is not rigid enough for effective manipulation, and side-to-side motion is very difficult if not impossible to effect due to inadequate rigidity, lack of an ergonomic handle and the shape of the device. FIGS. 2A and 2B, illustrating the use of a HUMI-type manipulator inserted in a patient uterus 60, clearly illustrate these shortcomings.

A more preferable approach to uterine manipulation employs an instrument having a rotatable hook (tip) or finger mounted at a pivot point proximate the cervical os, as provided by the Valtchev Uterine Mobilizer, one version of which is disclosed in U.S. Pat. No. 4,022,208. Such devices allow much easier and more effective manipulation of the uterus over a somewhat wider range of motion, although such is still severely limited due to the linkage employed to rotate the hook. However, the Valtchev manipulator persists with the use of a tenaculum to grasp the cervix (although the risk of uterine perforation is significantly reduced by the effective manipulation capability provided by the pivot location's proximity to the os). Furthermore, the instrument's cost and complexity constitute a serious impediment to widespread use, and the reusable nature of the device causes cleaning problems due to the use of a long spring and cannula and the presence of numerous crevices on the surface of the device.

Another, more recent development in uterine manipulators is disclosed in U.S. Pat. No. 5,237,985. The so-called "uterine retractor" of the '985 patent is depicted in several different forms, one with a pistol-grip arrangement at the proximal end of an elongated rod and an articulated mechanical linkage to cause rotation of a retractor finger pivoted at the distal end, and a second with a rotatable handle or knob at the proximal end of an elongated rod driving a retractor finger on a drum pivoted at the distal end through one or more wires secured at one end to the handle and at the other end to the drum. These devices have a fairly large number of parts, and in reusable form as disclosed are costly, complex and present the same contamination and cleaning problems as the Valtchev device. Moreover, the rotational range of motion about the pivot point is constrained to about 115° due to the nature of the drive linkages employed between the proximal and distal ends of the elongated rods to pivot the retractor finger, and substantial retroversion of the finger is not achievable. Due to the design of the drive linkage, the force applied by the user to rotate the handle or knob is unevenly transmitted to the drum over the rotational extent of movement of the retractor finger. The fact that the drive linkage "pushes" as well as pulls the drive wires secured to the drum and to the handle or knob requires the use of spacers or guides and limit stops to prevent binding and kinking of the wires and collapse of the drive linkage, particularly at its rotational extremes. In addition, the device of the '985 patent employs a spring-loaded ball or plunger biased into a plurality of sockets positioned at a common radius about the rotational center of the handle or knob to produce a "ratcheting" effect to provide the user with an indication of rotational movement of the drum. However, the holding force of the foregoing assembly is insufficient to maintain the uterus in an elevated position, thus requiring an extra staff member to grasp and immobilize the handle or knob to maintain the uterus in any unnatural position.

Also disclosed in the '985 patent are several embodiments of retractor fingers for use in association with the manipulator at the distal end thereof, several of the embodiments including a lumen-fed balloon, and optionally a second lumen for hydrotubation. In one embodiment, a third lumen houses a rigid structural member within the center of the retractor finger. As each lumen must be sufficiently large to perform its intended function and an adequate membrane must surround each lumen, the diameter of the tri-lumen stem is sufficient to require significant dilation of most patients. The result is trauma to the patient and added time and expense to the surgical procedure.

Another recently-developed uterine manipulator is the Gregersen U-Elevator offered by Karl Storz-Endoskope, which comprises a U-shaped rod having a cone for insertion into the uterus at one end and a weighted handle at the other end, a lumen for dye injection running from the handle and through the rod and the cone. The device permits the patient to lie in a normal position on her back, and the handle may be grasped by the surgeon to manipulate the uterus. However, the U-Elevator device is expensive and suffers from the inability to manipulate a tip assembly (in this case the cone) independently of the entire device, and the severe U-shape of the device limits its range of movement.

Although progress has been made in the art as noted above, all existing uterine manipulators known to the inventors herein possess significant disadvantages and limitations. With the increasing pressure for cost containment in medical treatment and the increasing popularity of laparoscopic gynecological procedures moving to outpatient clinics and GYN offices, a cost-effective uterine manipulator having enhanced manipulation capability and ease of use would be very attractive to the medical profession.

SUMMARY OF THE INVENTION

The present invention provides an effective, economical, easy to use uterine manipulator with superior performance to state of the art manipulators known to the inventors.

A first preferred embodiment of the present invention includes an insertion rod with integral handle extending perpendicularly or at a slight off-perpendicular angle at the proximal end of the rod. A manipulator tip assembly for insertion into the uterus is mounted on a tip support pivoted or hinged to the distal end of the insertion rod about an axis perpendicular thereto, the tip support also having a second similarly oriented pivot or hinge offset from the first for securing one end of a drive rod thereto. The drive rod extends from the tip support toward the proximal end of the insertion rod, where it is hinged to a retractor lever movable toward and away from the handle, such lever movement preferably also being pivotal. Movement of the retractor lever toward and away from the handle results in rotation the of tip support and of the tip assembly mounted thereon. A retractor locking pawl is associated with the handle and engages the retractor lever with a suitable structure to permit precise rotational positioning of the tip assembly as well as the ability to maintain the desired position of the tip assembly throughout its rotational range. It is preferred that all major components of the manipulator be molded plastic, and that the insertion rod, handle, retractor lever, locking pawl and drive rod be integrally molded, with the hinge points between the retractor lever and the handle and between the drive rod and the retractor lever being integral, "living" hinges of smaller cross-section plastic to accommodate the required limited pivotal movement without the necessity of hinge pins and other components.

A second preferred embodiment of the present invention includes an elongated, hollow insertion rod having an enlarged or flared proximal end for receiving a substantially perpendicularly-oriented, rotatable drive knob having a drive gear at one end thereof disposed within the insertion rod. The distal end of the insertion rod carries a tip support pivoted about an axis perpendicular to that of the insertion rod and also perpendicular to the rotational axis of the drive knob and drive gear, the tip support having associated therewith a laterally adjacent slave gear pivoted about a common axis and carrying a manipulator tip assembly thereon. An endless, toothed drive belt extends about both the drive gear of the drive knob and the slave gear of the tip support, the drive belt being twisted substantially 90° between the drive gear and the slave gear to accommodate their perpendicular axes. An alternative belt-driven embodiment is also disclosed.

A third preferred embodiment of the present invention employs a secondary drive axle contained and extending longitudinally within the insertion rod and rotatable to drive the slave gear of the tip support by a relatively perpendicular drive knob via a primary drive axle and gear within a handle at the proximal end of the insertion rod. If desired, the drive knob may be coaxial with and secured to the insertion rod drive axle to eliminate the need for a drive knob drive gear and drive axle slave gear.

Two of the three of the preferred embodiments of the uterine manipulator, by virtue of their tip drive design, afford a much greater rotational range of motion about the distal end of the insertion rod (preferably about 120° in anteversion and about 70° in retroversion) between the maximum anteverted and retroverted positions of the manipulator tip assemblies. This range of motion is significant in that the 120° anteverted position plus the geometry of the uterine manipulator of the present invention allows the uterus to be trapped between the manipulator tip assembly and the insertion rod for positive, non-traumatic, free-floating interaction and engagement between the device and the uterus, while the extreme retroverted position of the manipulator tip assembly promotes easier insertion of the tip assembly through the cervix into the uterus and permits manipulation of the uterus for better visibility of the bladder without rotating the device about the axis of the insertion rod.

It is preferred that all of the embodiments of the uterine manipulator of the present invention be primarily fabricated from suitable injection-molded plastic so as to render them inexpensive and therefore disposable after a single use.

The present invention also comprises a manipulator tip assembly having several embodiments, all of which possess a soft tip and balloon at the distal end thereof for firm retention of the tip assembly within the uterine cavity and to provide an effective seal for retention of dye and to protect the uterus from perforation. One embodiment employs two lumens, one for balloon inflation and another for dye injection, while a second embodiment uses a single lumen in combination with a pressure-actuated valve to inflate the balloon and inject dye after balloon inflation. The embodiments allow for one or two lumens within a small-profile rigid structural sleeve which can be inserted into the uterus of most patients with little or no cervical dilation.

DETAILED DESCRIPTION OF THE PREFERRED EMBODIMENTS

Figure 3A:
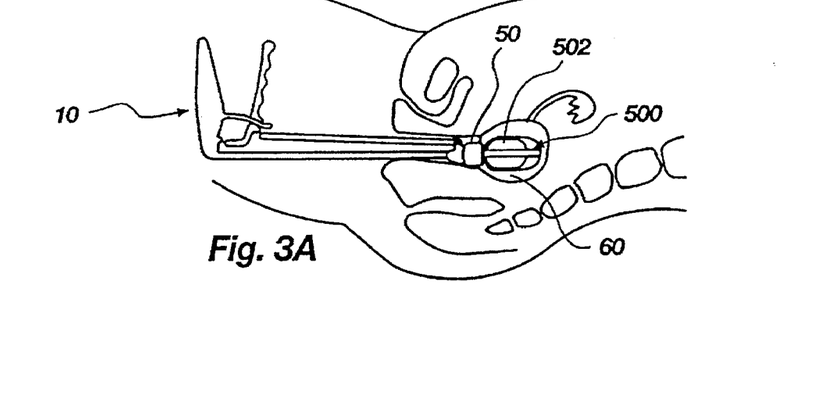
FIGS. 3A and 3B are schematic illustrations of a first preferred embodiment of the uterine manipulator of the present invention in use.
Figure 3B:
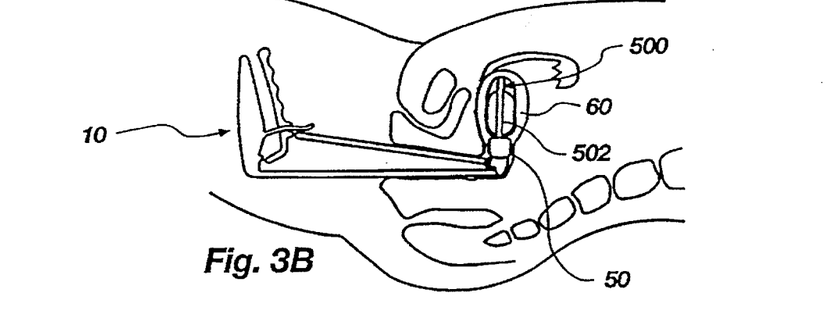
Figure 4:
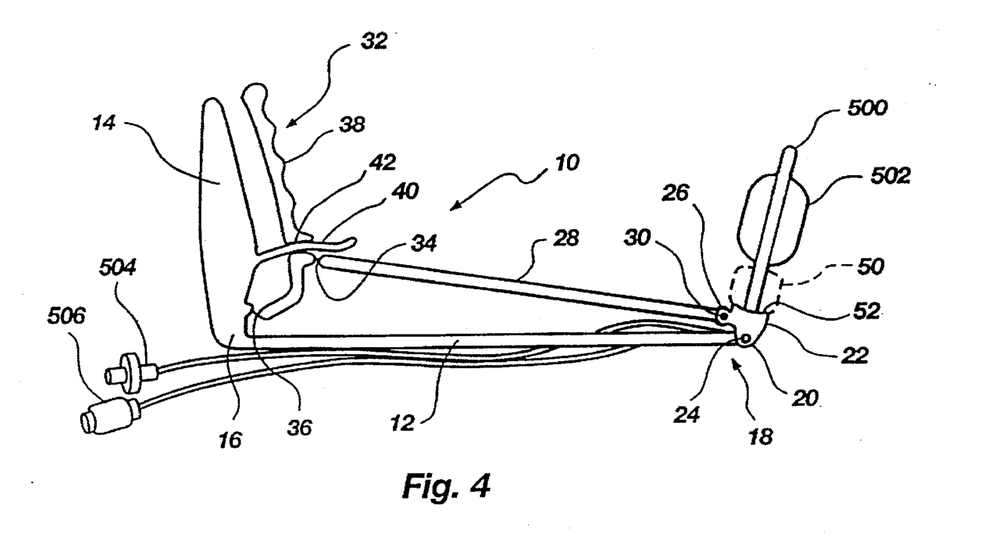
FIG. 4 is a side elevation of the first preferred embodiment of the uterine manipulator of the present invention.

Referring now to FIGS. 3A, 3B and 4 of the drawings, a first preferred embodiment 10 of the uterine manipulator of the present invention is illustrated. With specific reference to FIG. 4, manipulator 10 comprises a rigid, elongated insertion rod 12 having an integral handle 14 substantially perpendicular thereto at the proximal end 16 thereof for grasping by the practitioner during a procedure. The distal end 18 of insertion rod 12 includes an aperture therethrough oriented substantially perpendicularly to the rod axis, and also to the handle 14. A first yoke 20 of tip support 22 extends over the distal end 18 of rod 12 on both sides thereof, tip support 22 being rotatably secured to insertion rod 12 by pin 24, which extends through the rod aperture and through aligned apertures in yoke 20 to form a first hinge structure. A second yoke 26 of tip support 22, offset from first yoke 20 on the handle side of insertion rod 12, extends over the distal end of drive rod 28 on both sides thereof and is rotatably secured to drive rod 28 by pin 30, which extends through an aperture at the distal end of drive rod 28 and through aligned apertures in second yoke 26 to form a second hinge structure. The axis of pin 30 is aligned with that of pin 24. The proximal end of drive rod 28 is hinged to retractor lever 32 at point 34, one end of retractor lever 32 being hinged at 36 to handle 14, the other end of retractor lever 32 being free. Retractor lever 32 includes a scalloped leading face 38 to promote a firm grip by the practitioner. Locking pawl 40 extends from handle 14 through a slot 42 in the side surface of retractor lever 32, cooperating ratchet teeth (not shown) on the exterior of locking pawl 40 and the interior of slot 42 permitting defined incremental rotational movement and positive positioning of a manipulator tip assembly generally designated as 500 mounted on tip support 22 by insertion in a suitable aperture in the latter. Alternatively and in lieu of a ratchet, sufficient friction may be provided between locking pawl 40 and slot 42 to prevent slippage. As shown, manipulator tip assembly 500 preferably includes a balloon 502. As shown in broken lines at 50, an os stop of toroidal or other suitable shape may be slipped over tip assembly 500 to limit the depth of penetration into a smaller uterus. Various sizes (depths) of os stops are contemplated, in order to enable the practitioner to select a substantially exact extent of penetration by tip assembly 500. Os stop 50 fits snugly over tip assembly 500, and is supported from beneath by annular support surface 52 on tip support 22 surrounding the aperture into which tip assembly 500 is inserted. Tubes 504 and 506 lead to the proximal end of tip assembly 500 at tip support 22, tube 504 for dye injection through tip assembly 500 and tube 506 for inflation of balloon 502.

It is preferred for low cost and hence disposability that the major components of uterine manipulator 10 be injection molded of a suitable plastic, such as polyurethane. It is also preferred, as shown in FIG. 4, that insertion rod 12, handle 14, drive rod 28, retractor lever 32 and locking pawl 40 be molded as a single, integral unit, hinge points 34 and 36 being "living" hinges of small material cross-section, which permits adequate flexibility for the limited range of rotational motion required at those two points. Tip support 22 is preferably injection molded plastic and is assembled with the remainder of manipulator 10 with hinge pins 24 and 30, which may be of a suitable metal such as stainless steel or of a suitably robust, reinforced (nylon, fiberglass, graphite) plastic. Pins 24 and 30 may be press fit through the apertures in their respective cooperating yokes, the rod apertures being larger in diameter than the pins for free relative movement of the various components. In lieu of pins, it is contemplated that insertion rod 12 and drive rod 28 may be molded with laterally outwardly extending protrusions which would snap into the yoke apertures and serve as hinge pins, thus eliminating any metal parts. Of course, the yokes could also be formed with inwardly-extending protrusions to snap into apertures or recesses on rods 12 and 28 to serve the same purpose.

Referring now to FIGS. 3A and 3B of the drawings and comparing same to FIGS. 2A and 2B, it will be readily apparent that the uterine manipulator 10 of the present invention, with the tip support assembly pivoted proximate the cervical opening, permits easier and much more effective manipulation of the uterus 60 over a wide range of motion afforded by the drive linkage for the tip support, and also reduces the risk of uterine perforation. Balloon 502, when inflated, firmly secures the manipulator in the uterus. The balloon 502, combined with an os stopper 50 of suitable height, assures that uterus 60 is held securely but gently between the tip assembly 500 and the insertion rod 12 and that no perforation, tearing or over-insertion is possible.

Figures 5, 5A, 5B, 5C, 5D, 5E:
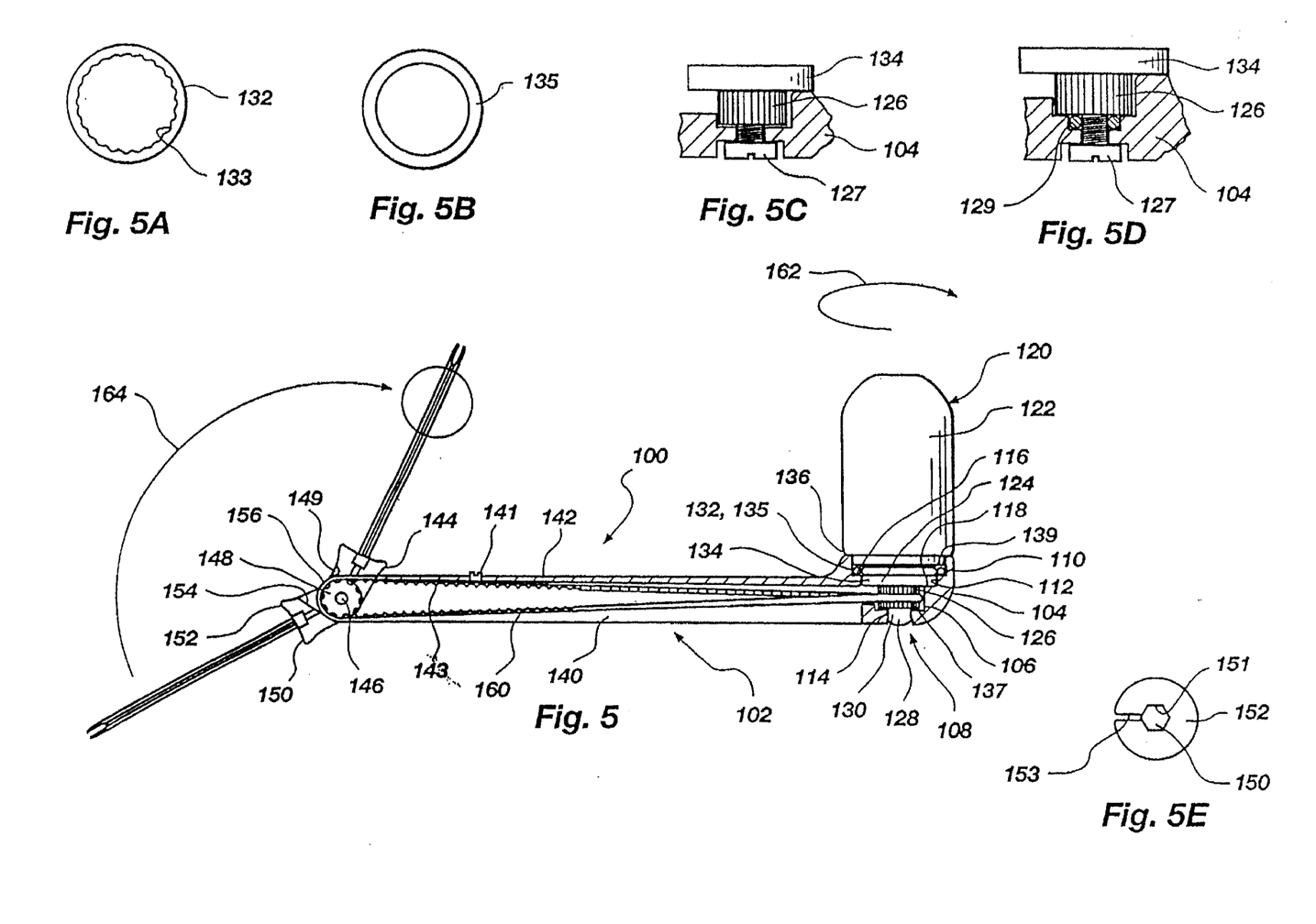
FIG. 5 is a side, partial sectional elevation of a second preferred embodiment of the uterine manipulator of the present invention.
FIG. 5A is an enlarged top elevation of a ratchet ring employed in the embodiment of FIG. 5.
FIG. 5B is an elevation of a washer employable to provide friction in the drive linkage of the embodiment of FIG. 5 in lieu of the ratchet ring of FIG. 5A.
FIG. 5C is an enlarged side sectional elevation of a screw or drive pin arrangement for providing friction in the drive linkage of the embodiment of FIG. 5.
FIG. 5D is an alternative screw or pin arrangement to that of FIG. 5C, employing a washer as a friction element.
FIG. 5E is a top elevation of a tip support of the present invention, usable in the embodiment of FIG. 5.

Referring to FIG. 5 of the drawings, a second preferred embodiment 100 of the uterine manipulator of the present invention is illustrated. Insertion rod 102 of manipulator 100 is hollow and has a flared or enlarged proximal end 104 defining a drive gear chamber 106, the bottom of chamber 106 having an aperture 108 therethrough and the upper end of the chamber having an aligned, much larger aperture 110 with stepped counterbore 112. Bottom aperture 108 includes an inwardly-extending annular protrusion 114. Aperture 110 defines an annular shelf 116 at its periphery, and counterbore 112 defines a substantially annular shelf 118. Drive knob 120 has a major portion 122, which may be knurled or otherwise roughened or contain asymmetrical lobes to enhance the user's grip, and a minor portion 124 which extends into proximal end 104 of insertion rod 102. Minor portion 124 includes toothed drive gear 126 having axially extending therefrom axle 128, which has enlarged head 130 at the tip thereof. Axle 128 extends through the bottom aperture 108 of drive gear chamber 106, annular protrusion 114 engaging enlarged head 130 to rotatably secure drive knob 120 to insertion rod 102. A ratchet ring 132 may be disposed and secured in aperture 110 (as by press fit or with an adhesive) and supported from below by shelf 116, ratchet ring 132 (see FIG. 5A) including teeth 133 on the interior thereof for engaging protrusions on the adjacent exterior circumference of drive knob 120, which protrusions may be integrally formed with drive knob 120 or comprise separate pins secured in apertures drilled or formed in the drive knob if a more wear-resistant material than that of drive knob 120 is desired. Counterbore 112 and shelf 118 at the bottom thereof receive, and respectively laterally and axially support, drive gear base 134 on drive knob 120. The upper extent of aperture 110 receives and laterally supports the lowermost extent 136 of major portion 122 of drive knob 120. Thus, the position of drive knob 120 with respect to insertion rod 102 is fixed by the enlarged head 130 of axle 128, and drive knob 120 is supported against lateral forces at three axially-spaced locations to prevent cocking when drive knob 120 is twisted and is also supported axially by annular shelf 118 and the bottom of drive gear chamber 106.

It is also contemplated that a ratchet assembly may be eliminated from the present invention by providing sufficient frictional forces between the moving parts of the manipulator to ensure retention of the tip assembly and thus of the uterus in any desired rotational position.

The side walls 140 and upper wall 142 of insertion rod 102 define an open, elongated passage of U-shaped cross section. The distal ends of side walls 140 include coaligned apertures defining an axis perpendicular to that of insertion rod 102. Tip support 144 having a pin 146 extending therethrough and through the side wall apertures is rotatably mounted between side walls 140. Adjacent tip support 144 and between side walls 140, pin 146 also carries coaxial, toothed slave gear 148, which rotates with tip support 144.

Tip support 144 includes an aperture 150 (see FIG. 5E) for receipt of a manipulator tip assembly 500, aperture 150 being surrounded by a substantially annular support surface 152 for an os stop (not shown), such as has previously been described. It will be noted that aperture 150 is illustrated in FIG. 5E as substantially hexagonal, a feature which promotes a firm press fit grip of the round shaft or tube of manipulator tip support assembly 500. By sizing the flat-to-flat distance of aperture 150 to be slightly less than that of the outer diameter of the tip assembly shaft end to be inserted, insertion of the manipulator tip assembly 500 results in deflection of the shaft and concentration of force between the substantially tangential contact between flats 151 and the exterior of the tip assembly shaft or tube. Slot 153 extending from aperture 150 to the outer edge of support surface 152 accommodates tubes (see FIGS. 4, 9, 10 and 11) emanating from the proximal end of the manipulator tip assembly 500 so that such may then run back along insertion rod 102, either secured thereto or in an unconstrained manner, when the manipulator is inserted.

Tip support 144 also includes a cam surface 154 for limiting and defining the rotational range of motion of tip support 144 via contact with one or both side walls proximate their rounded ends 156 at the top and bottom thereof. An endless, toothed drive belt 160 runs about drive gear 126 and slave gear 148 and extends therebetween, drive belt 160 being twisted substantially 90° in its run between the gears to accommodate their mutually perpendicular orientations.

To prevent binding of drive belt 160 and inadvertent slippage thereof from slave gear 148, tip support 144 includes a step or tooth 149 to trap belt 160 against slave gear 148 at a single point, located to permit the full range of rotational motion of tip assembly 500 and lift-off of belt 160 from slave gear 148 as the belt moves and rotates the gear and the tip support. The distal end of drive belt 160 is prevented from lifting off of drive gear 126 by the close proximity of the inner wall of drive gear chamber 106.

To rotate manipulator tip support 144 (and tip assembly 500), drive knob 120 is turned or twisted, as shown at 162, about its axis. Clockwise rotation as depicted at 162 will result in clockwise rotation of manipulator tip support 144 as shown at 164 to its most anteverted position. Counterclockwise drive knob rotation will return tip support 144 to its most retroverted position. The previously-described ratchet mechanism will hold tip assembly 500 in its desired rotational position until a significant torsional force is again applied by the practitioner to the drive knob 120.

As previously noted, friction in the drive linkage may be employed to maintain tip assembly 500 in its desired position in lieu of a ratchet mechanism. For example (see FIGS. 5, 5B), a relatively soft elastomeric washer 135 may be inserted in aperture 110 and rest on annular shelf 116, washer 135 sized, when compressed between the outer wall of aperture 110 and the adjacent exterior surfaces 137 and 139 of drive knob 120, to provide adequate frictional force to prevent undesired rotation of drive knob 120 and therefore movement of tip support 144. A suitable frictional force preferably ranges from about 5 oz. to about 2 lb, as measured via the attempted rotation of a 6–7 cm long tip assembly 500 via force applied to the free end thereof.

A further alternative to provide a holding force against inadvertent rotation of tip support 144 (see FIG. 5) is the use of an adjustable set screw 141 threaded into bore 143 of upper wall 142 of insertion rod 102 at a suitable location near the distal end thereof, the inner tip of the set screw bearing against the exterior of drive belt 160 to tension same. Set screw 141 might also be placed in a side wall 140 at a suitable location nearer the proximal end 104 of insertion rod 102.

Yet another alternative to provide suitable frictional force in the drive linkage for the tip assembly is the use of an adjustment screw 127 (see FIG. 5C) threaded into a bore at the bottom of toothed drive gear 126 alone or (see FIG. 5D) in combination with a compressible washer 129. Screw 127 may in fact comprise a self-locking drive pin to facilitate assembly of the device.

If desired, the drive knob 120 and proximal end 104 of the insertion rod 102 may be suitably marked and graduated to indicate the exact rotational position of the tip assembly 500. The bottom of insertion rod 102 may be closed, if desired, with a cover plate. It should be noted that the lowermost edges of the two laterally-spaced side walls 140 of insertion rod 102, in combination with the flared or enlarged proximal end thereof, permit manipulator 100 to be placed on a flat, horizontal surface without tipping over for easy grasping of drive knob 120.

It is preferred that the major components of manipulator 100 be injection molded of suitable plastic for cost savings, thus permitting disposability of the device. Pin 146 is preferably of stainless steel or robust plastic (reinforced with fiberglass or graphite, if desired), and drive belt 160 of kevlar-reinforced polyurethane. Components of manipulator 100 may preferably be integrally molded, such as the tip support 144 with slave gear 148, or drive knob 120 with drive gear 126.

Figure 6:
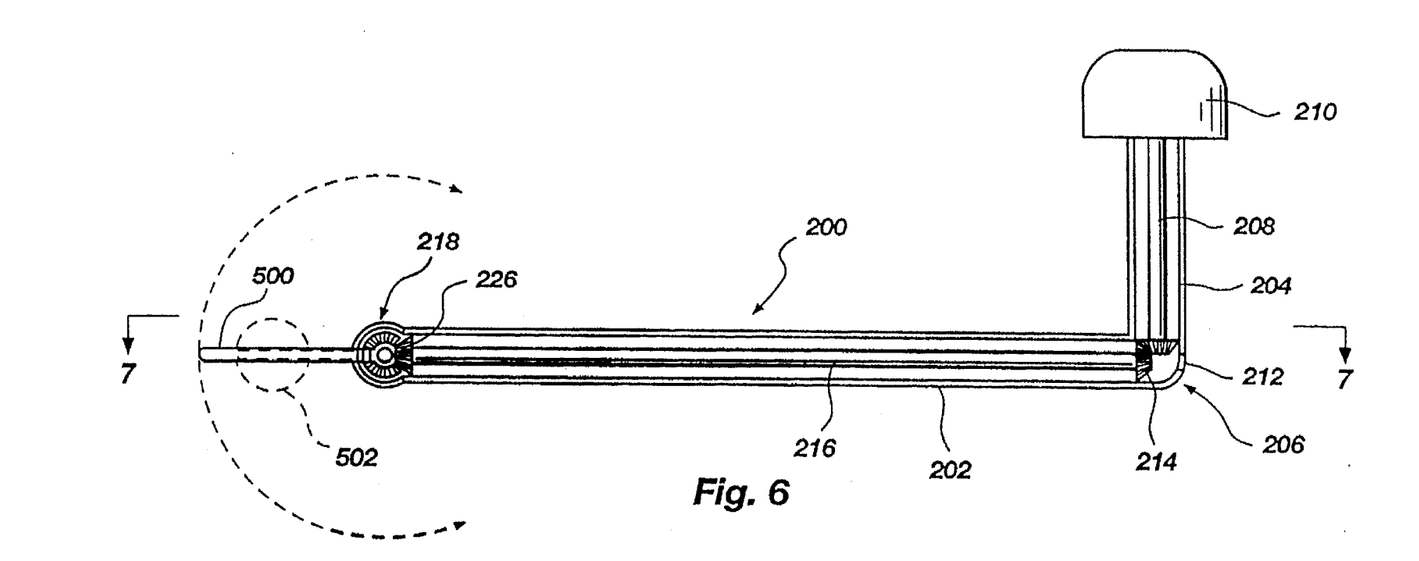
FIG. 6 is a side, partial sectional elevation of a third preferred embodiment of the uterine manipulator of the present invention.
Figure 7:
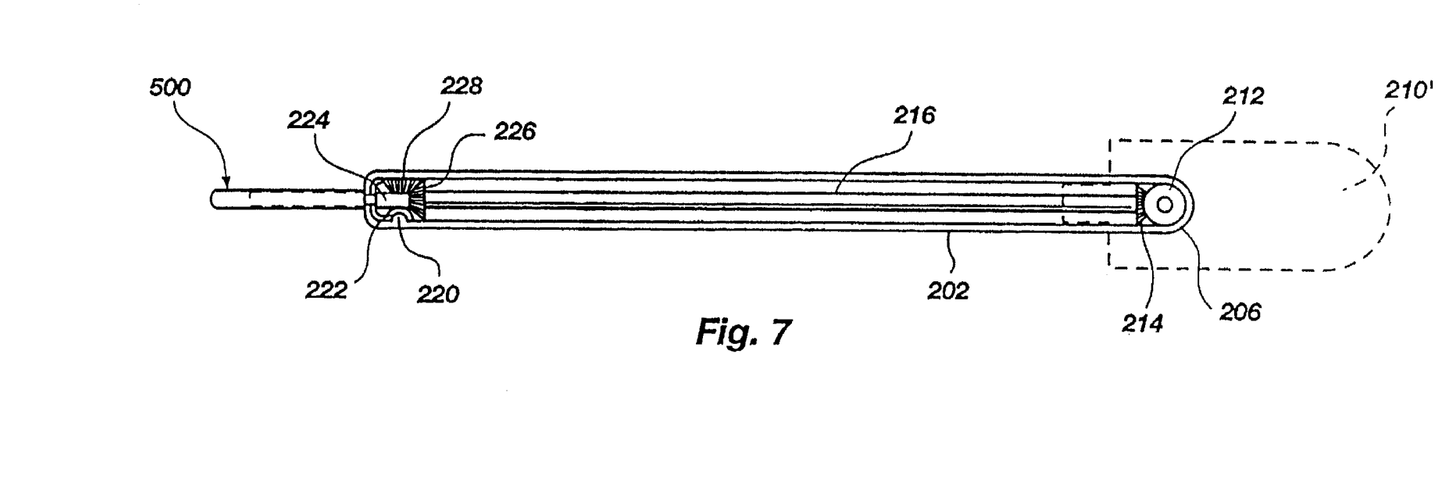
FIG. 7 is a top, partial sectional elevation of the third preferred embodiment, taken along lines 7—7 in FIG. 6.

Referring to FIGS. 6 and 7 of the drawings, a third preferred embodiment 200 of the uterine manipulator of the present invention is illustrated. Manipulator 200 includes a hollow, tubular insertion rod 202 having a perpendicular elbow segment 204 at the proximal end 206. Elbow segment 204 receives a rotatable primary drive axle 208 secured to drive knob 210, primary drive axle 208 having toothed, bevelled gear 212 at its other end. Drive gear 212 in turn engages bevelled slave gear 214, to which is secured secondary drive axle 216 extending through insertion rod 202 to its slightly bulbous distal end 218, where two aligned, inwardly-extending protrusions 220 on the interior of insertion rod 202 engage coaligned recesses 222 on tip support 224 to permit secured rotation thereof about an axis perpendicular to that of insertion rod 202. Secondary drive axle 216 carries a toothed, beveled drive gear 226 at its distal end, drive gear 226 engaging slave gear 228 of tip support 224. Due to the close fit of the drive and slave gears within insertion rod 202, the circumference of the gears providing an integral bearing structure, no additional bearings are required to support the rotating drive axles. Drive knob 210 and the free end of elbow segment 204 may be formed with a matching annular groove or ridge on one component, and engaging protrusions on the other, whereby the two components, and primary drive axle 208, will be maintained in position. Such a configuration may be combined with or separate from a ratchet mechanism to provide a precise positioning and locking capability for the manipulative tip 500 as previously discussed. Secondary drive axle 216 is secure against removal from insertion rod 202 by its contact with tip support 224, which is snapped into the distal end 218 of insertion rod 202 between protrusions 220.

In lieu of a drive knob 210 perpendicular to insertion rod 202, it is contemplated that a drive knob 210' may be made coaxial and integral with secondary drive axle 216 as shown in broken lines, thus eliminating gears 212 and 214 and simplifying and reducing the cost of the device.

All components of manipulator 200 are preferably injection-molded plastic and assembled together by snap-fit without the use of adhesives or fasteners, thus rendering this embodiment extremely inexpensive. Moreover, given the use of an axle drive instead of a belt drive, the secondary drive axle 216 may be made hollow and used to contain tubes for inflation of balloon 502 on tip assembly 500.

Figure 8:
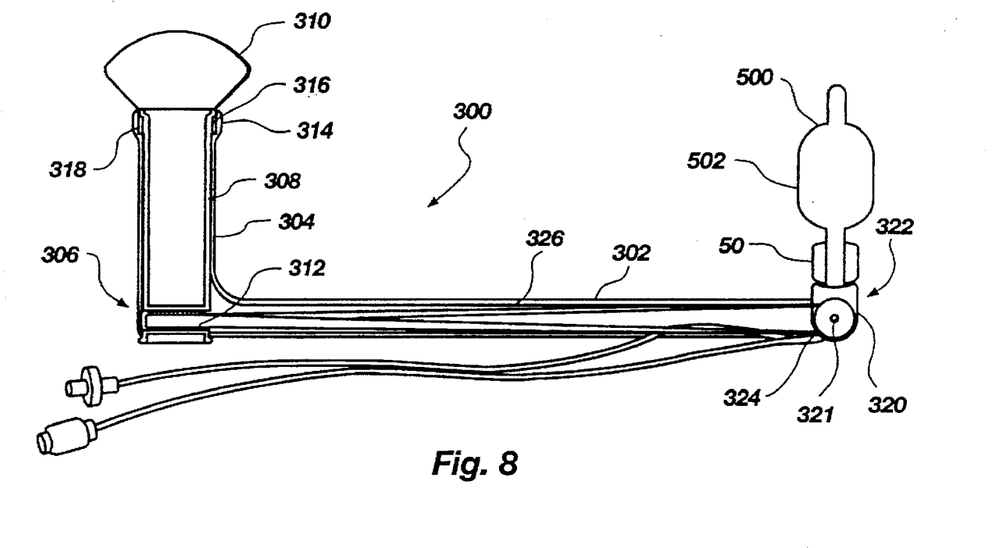
FIG. 8 is a side, partial sectional schematic elevation of an alternative version of the second preferred embodiment of the uterine manipulator of the present invention.

FIG. 8 depicts an alternative second embodiment 300 of the uterine manipulator of the present invention. Manipulator 300 includes a hollow, elongated insertion rod 302 having an enlarged perpendicular elbow comprising a handle segment 304 at its proximal end 306. Handle segment 304 receives a drive knob 308, the head 310 of which protrudes from the top of handle segment 304 for turning by the user. Drive knob 308 extends into handle segment 304 to the bottom thereof, whereat a drive gear 312 at the innermost end of drive knob 308 is aligned with the major, elongated portion of insertion rod 302. A collar 314 at the top of handle segment 304 includes ratchet teeth 316 on the interior thereof, which teeth 316 engage protrusions 318 on the exterior of drive knob 308 to permit positive control of the rotational movement and position of the manipulator tip assembly 500. Alternatively, collar 314 may merely define an annular, smooth-walled compartment drive knob 308 having a smooth-walled exterior within the compartment, and a soft elastomeric washer may be inserted in the compartment and compressed between the collar 314 and drive knob 308 to provide adequate frictional resistance to rotational movement of drive knob 308 and thus of tip assembly 500. As with manipulator 200, drive knob 308 may be designed to snap together with handle segment 304 to prevent the withdrawal thereof, or be fastened to handle segment 304 with a self-locking drive pin or screw. Tip support 320 is pivotally mounted on pin 321 at the distal end 322 of insertion rod 302, and includes a slave gear 324. Endless toothed belt 326 extends about both drive gear 312 and slave gear 324, both of which are also toothed to engage the belt teeth. As with manipulator 100, belt 326 is twisted substantially 90° to accommodate the mutually perpendicular axes of the gears. It will be noted that this embodiment of the invention includes a large drive gear diameter, relative to the slave gear, so that the rotation of drive knob 308 will result in a much greater rotational displacement of tip support 320. However, a smaller drive gear may be employed for ease of rotation by the user.

As with previously-described embodiments of the invention, the major components of manipulator 300 are molded of plastic, and assembled with a minimum of additional components, in this case drive belt 326 and pivot pin 321.

Figure 9:
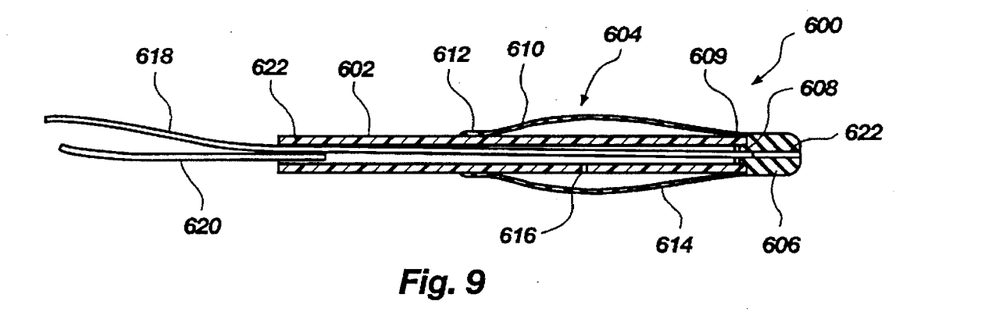
FIG. 9 is a side sectional elevation of a first preferred embodiment of a manipulator tip assembly according to the present invention.

Referring now to FIG. 9 of the drawings, a first preferred embodiment 600 of the previously generically-described manipulator tip assembly 500 of the present invention will be described in detail. Manipulator tip assembly 600 includes a substantially rigid tubular body 602, preferably of stainless steel tubing or most preferably of a rigid, preferably reinforced (nylon, fiberglass, graphite) plastic. A liquid injection-molded, tubular, resilient silicone envelope 604 with a substantial silicone mass 606 for softness at the distal end of the tip assembly 600 is disposed over the distal end of tubular body 602 and interior axial protrusion 608 of mass 606 is received within the distal end of body 602. The skirt 610 of envelope 604 extends from mass 606 over the exterior of tubular body 602. The envelope 604 is bonded to tubular body 602 on the latter's exterior, as by a suitable adhesive such as a room-temperature vulcanizing silicone (RTV), adjacent mass 606 at 609 and at the free end 612 of skirt 610, to form a closed chamber defining a balloon 614 inflatable though aperture 616 in the wall of tubular body 602. Two lumens, designated 618 and 620 respectively, are employed in this embodiment. Lumen 618 extends from the proximal end of tubular body 602 into soft mass 606 at the distal end thereof, where it is inserted in axial passage 622 of soft mass 606 and sealed thereat with a suitable adhesive, again such as RTV. Lumen 618 is employed for dye injection into the uterus through the manipulator tip assembly 34. Lumen 620 enters the proximal end of tubular body 602, but terminates shortly thereafter, feeding fluid into the interior of tubular body 602 until the fluid, under suitable pressure, inflates balloon 614 through aperture 616. The small gap between the exteriors of lumens 618 and 620 at the proximal end of tubular body 602 and the interior wall of the latter are sealed with RTV adhesive or other suitable substance.

In its uninflated state, balloon 614 does not protrude radially by any perceptible degree from tubular body 602. It has been found that the outer diameter of the manipulator tip assembly with uninflated balloon should not exceed substantially 4.5 mm, so as to avoid the use of a cervical dilator during insertion of the tip assembly. The soft mass at the tip of the assembly prevents uterine perforation, while tubular body 602 possesses the strength required for effective manipulation of the uterus. It is further preferred that the balloon 614 be capable of inflating to a diameter of 2 cm in order to effectively seal off the cervical opening and prevent dye leakage during a procedure. Of course, different lengths and diameters may be provided to accommodate a variety of uteruses and cervical openings.

Figures 10, 10A, 10B:
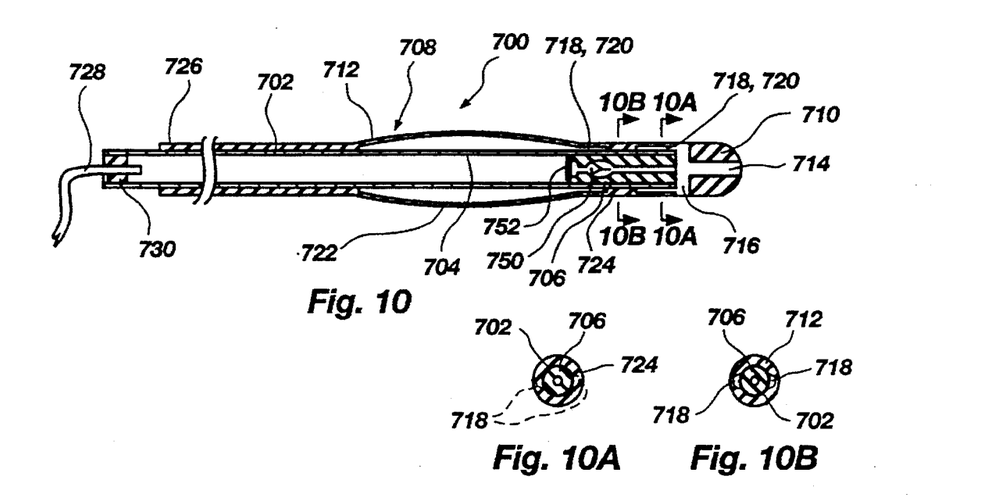
FIG. 10 is a side sectional elevation of a second preferred embodiment of a manipulator tip assembly according to the present invention.
FIGS. 10A and 10B are sectional views taken transversely through FIG. 10 along section lines A—A and B—B, respectively.

Referring to FIGS. 10, 10A and 10B of the drawings, a second preferred embodiment 700 of the manipulator tip assembly of the present invention will be described. Embodiment 700 includes a rigid, tubular body 702, preferably of stainless steel, which includes a balloon inflation aperture 704 in the side wall thereof. The distal end of body 702 is occluded with press-fit plug 706 of silicone or other suitable material, and a resilient, tubular envelope 708 of silicone having a soft mass 710 is disposed over tubular body 702, with the skirt 712 of envelope 708 extending over the exterior of tubular body 702 for a substantial distance, and preferably to a location proximate the proximal end of tubular body 702. Soft mass 710 includes an axial dye injection channel 714 and an intersecting lateral channel 716 adjacent plug 706. Longitudinal grooves 718 molded in a first portion of the interior wall of envelope 708 adjacent soft mass 710 define, with the exterior of tubular body 702, dye feed channels 720 extending from the interior of a second, thin-walled portion of skirt 712 defining balloon 722 to dye injection channels 714 and 716. Dye feed channels 720 are interrupted and normally occluded by resilient annular valve band or segment 724 integrally molded in skirt 712. Valve band 724, being of uniform thickness unlike the longitudinally adjacent portions of skirt 712 having grooves molded therein, has greater resistance under internal pressure to outward displacement away from tubular body 702, and thus serves as a valve to prevent dye movement into the dye injection channels until a desired pressure has been reached. The third portion or proximal end 726 of skirt 712 is extended, as previously noted, and is of greater wall thickness than in the area of balloon 722, so as to form a resilient, pressure-tight seal with tubular body 702 without the use of adhesive. A single fluid (dye) injection lumen 728 is employed in this embodiment, and feeds to the interior of tubular body 702, the gap between the lumen exterior and the interior wall of tubular body 702 at the latter's proximal end being closed by a plug 730 having the lumen extending therethrough, or by a hardenable adhesive or other bonding substance.

The extended silicone envelope 708 fits tightly over the exterior of tubular body 702 so that no adhesive is required for a seal and extends over tubular body 702 except where the tip assembly is attached to the manipulator. In operation, when fluid is introduced through lumen 728, the thin-walled balloon 722 inflates via aperture 704 at a suitable pressure, for example 100–200 mm Hg, and resilient valve band 724 subsequently moves away from tubular body 702 at a higher pressure, for example about 500 mm Hg, to permit dye to flow through dye feed channels 720 into dye injection channels 714 and 716 and out into the uterus of the patient.

As an alternative to grooves 718 and valve band 724 of second preferred embodiment 700, a central passage with one-way valve 750 (see also FIG. 10) might be employed to control the injection of dye into the uterus. A flapper valve 750 is one suitable design or one that opens at a particular geometry or orientation or, if a valve per se is not required, a pressure-rupturable diaphragm 752 may be employed.

Figure 11:
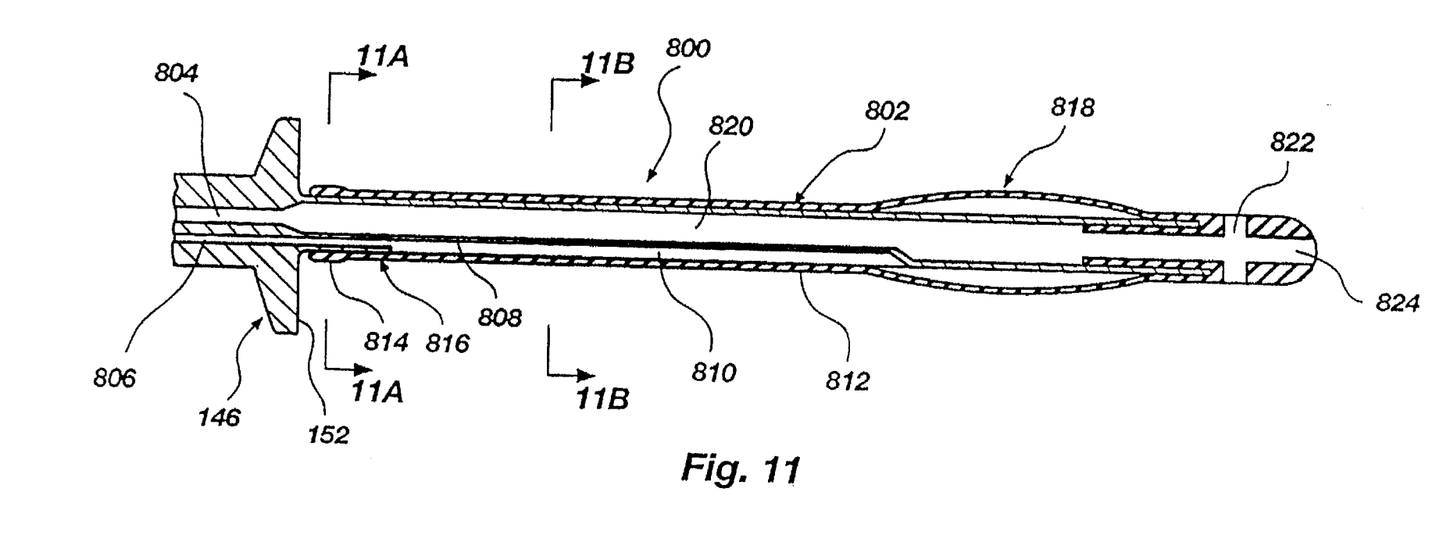
FIG. 11 is a side sectional elevation of a third preferred embodiment of a manipulator tip assembly according to the present invention in combination with a tip support.
Figure 11A:
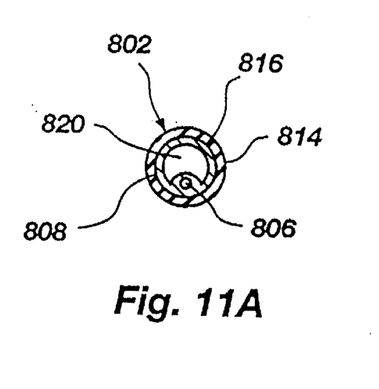
FIGS. 11A and 11B are sections taken along lines A—A and B—B in FIG. 11.
Figure 11B:
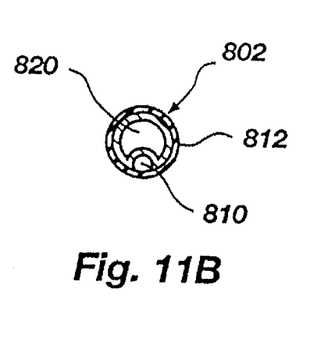

It is also contemplated that the tip support of the uterine manipulator of the present invention and tubular body or shaft (preferably fiberglass) of the manipulator tip assembly may be molded or otherwise formed on a single unit. In such an embodiment 800, as depicted in FIG. 11, tip support 146 would possess two lumens, one central lumen 804 extending to the interior of tubular body or shaft 802, and one offset lumen 806 which would extend longitudinally within and along the wall 808 of shaft 802 as a tunnel for a distance above annular support surface 152 and opening into a groove 810 in the exterior of shaft 802. With such a design, a tubular, resilient silicone envelope 812 may be placed over shaft 802 and frictionally, resiliently seal at band 814 therewith at ungrooved area 816. Thus, balloon 818 of envelope 812 may be inflated through lumen 806, and dye injected through lumen 804, into the interior 820 of shaft 802 and out of passages 822 and 824 into the uterus.

With the foregoing embodiment of the invention, the uterine manipulator may be cleaned, sterilized and reused with only the replacement of envelope 812 being required for re-use. It will also be appreciated that embodiment 800 may comprise the tip assembly above, without the integral tip support 146.

Each of the preferred embodiments of the manipulator tip assembly of the present invention may be employed with any of the embodiments of the uterine manipulator of the present invention.

It should also be noted that the second and third preferred embodiments of the uterine manipulator are capable of an extremely large range of motion, at least about 150° to preferably about 230°, in contrast to the previously-discussed limitations of Valtchev and the device of the '985 patent. Even more desirable, in contrast to the prior art devices, is the ability to antevert the tip assembly to about 120° and to retrovert the tip assembly to about 70°. As noted previously, the ability to non-traumatically trap the uterus between the manipulator tip assembly 500 and the insertion rod of the device is a major advantage of the extreme anteverted position, while the extreme retroverted position permits easy insertion of the tip assembly (there are, in fact, many retroverted uteruses) and manipulation (retroversion) of the uterus for better visibility of the bladder without rotation of the device. To achieve significant benefits with the manipulator of the present invention, the anteversion capability should be at least about 90°, and the retroversion capability at least about 30°.

While the present invention has been described in terms of certain preferred and alternative embodiments, it is not so limited, and those of ordinary skill in the art will readily appreciate that many additions, deletions and modifications to the illustrated and described embodiments may be made without departing from the scope of the invention as hereinafter claimed. For example, an untoothed drive belt with pulleys in lieu of gears may be employed; the drive belt may be pinned at a single location to the slave pulley and at another location to the drive pulley, the drive belt may be perforated instead of toothed, and engage protrusions instead of teeth on the gears; a positive, separate lock may be added to the ratchet; the rotatable drive knob may be disposed on an axis parallel to the pivot axis of the tip support for more natural grip and rotation by the practitioner, such an arrangement employing an untwisted belt; in the preceding design alternative, an articulated, tiltable drive knob may be employed to lock tip support in a second position after rotation of the tip assembly to its desired position, for easier manipulation of the device; eccentric slave gears or cams may be employed at the tip support to amplify or reduce tip assembly movement responsive to drive movement in certain ranges; and others.

What is claimed is:

1. A manipulator tip assembly for insertion into the uterus, comprising:

a resilient, tubular envelope including a mass of soft material at one end thereof having a passage therethrough from the interior to the exterior of said envelope and a thin-walled skirt extending from said soft material mass to the other end of said envelope;

a substantially rigid, tubular element inserted in said envelope, abutting and sealingly secured to said soft mass, in communication with said passage and extending beyond said skirt, which is sealingly secured thereabout in spaced relationship to said soft mass to define a balloon;

an inflation aperture extending through the wall of said tubular element to the interior of said balloon;

a first lumen extending into the interior of said tubular element and in communication with said passage; and a second lumen extending into the interior of said tubular element and in communication with said inflation aperture.

2. The manipulator tip assembly of claim 1, wherein said resilient tubular envelope is formed of silicone.

3. A manipulator tip assembly for insertion into the uterus, comprising:

a substantially rigid, tubular element occluded proximate one end thereof, and having an aperture through its side wall;

a resilient, tubular envelope including a mass of soft material at one end thereof having at least one fluid injection passage extending therethrough from the interior to the exterior of said envelope and a thin-walled skirt extending from said soft material mass to the other end of said envelope;

said skirt including a first tubular portion of a first wall thickness adjacent said soft material mass, a second tubular portion of a second wall thickness less than said first portion thickness and adjacent said first portion, and a third tubular portion of wall thickness greater than said second wall portion and adjacent thereto;

said envelope being disposed over said tubular element so that said soft mass is adjacent said occluded end and said skirt extends over said tubular element in resilient engagement therewith, said third skirt portion being resiliently sealed about the exterior of said tubular element, said second skirt portion being in communication with said side wall aperture to define a balloon;

a fluid feed passage extending from the interior of said tubular element to said at least one fluid injection passage;

a valve to control fluid flow through said fluid feed passage to said at least one fluid injection passage;

a lumen extending into said tubular element at its nonoccluded end; and a seal between the exterior of said lumen and the interior of said tubular element at a location between said nonoccluded end and said aperture.

4. The manipulator tip assembly of claim 3, wherein said resilient tubular envelope is formed of silicone.

5. The manipulator tip assembly of claim 3, wherein said fluid feed passage includes a longitudinally extending groove in said first tubular portion of said skirt and the exterior of said tubular element, and said valve includes a circumferentially extending ungrooved segment of said first tubular portion interrupting said groove.

6. The manipulator tip assembly of claim 3, wherein said fluid feed passage extends through one end of said tubular element and said valve includes a pressure-responsive structure.

7. A manipulator tip assembly for insertion into the uterus, comprising:

a substantially rigid, tubular element having a longitudinally extending tunnel passage in the sidewall thereof proximate one end thereof, said tunnel passage opening into a longitudinal groove on the exterior of said sidewall; and a resilient, tubular envelope including a mass of soft material at one end thereof having at least one fluid injection passage extending therethrough from the interior to the exterior of said envelope, and a skirt extending from said soft mass including a balloon portion of reduced wall thickness;

said envelope being disposed over said tubular element so that said soft mass is adjacent one end of said tubular element with said at least one fluid injection passage in communication with the interior thereof, said balloon portion surrounds said tubular element in communication with said groove, and said skirt extends over said tubular element past the point at which said longitudinally extending tunnel passage opens into said groove and resiliently, frictionally seals therewith.

8. The manipulator tip assembly of claim 7, wherein said skirt further includes an area of increased wall thickness extending over said tubular element in the area of said tunnel passage.

9. The manipulator tip assembly of claim 7, further including a tip support secured to said tubular element at the tunnel passage end thereof for attachment of said manipulator tip assembly to a uterine manipulator, said tip support including a first lumen therein in communication with said interior of said tubular element and a second lumen in communication with said tunnel passage.

* * * * *